US009890169B2

(12) United States Patent
Armani et al.

(10) Patent No.: US 9,890,169 B2
(45) Date of Patent: Feb. 13, 2018

(54) TRIAZOLINONE COMPOUNDS AS HNE INHIBITORS

(71) Applicant: CHIESI FARMACEUTICI S.P.A., Parma (IT)

(72) Inventors: Elisabetta Armani, Parma (IT); Carmelida Capaldi, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/375,281

(22) Filed: Dec. 12, 2016

(65) Prior Publication Data
US 2017/0166574 A1    Jun. 15, 2017

(30) Foreign Application Priority Data
Dec. 14, 2015    (EP) .................................. 15199816

(51) Int. Cl.
| C07D 487/04 | (2006.01) |
| A61K 31/519 | (2006.01) |
| A61P 11/06 | (2006.01) |
| A61P 11/08 | (2006.01) |
| A61P 17/06 | (2006.01) |
| A61P 37/08 | (2006.01) |

(52) U.S. Cl.
CPC ................... *C07D 487/04* (2013.01)

(58) Field of Classification Search
CPC .......................... C07D 487/04; A61K 31/519
USPC ....................... 544/263; 514/259.1
See application file for complete search history.

(56) References Cited

FOREIGN PATENT DOCUMENTS

| WO | 2010/078953 | 7/2010 |
| WO | 2011/110858 | 9/2011 |
| WO | 2011/110859 | 9/2011 |
| WO | 2013/037809 | 3/2013 |
| WO | 2014/095700 | 6/2014 |

OTHER PUBLICATIONS

Von Nussbaum et al. Bioorganic & Medicinal Chemistry Letters 2015, 25, 4370-4381.*
European Search Report in Application No. 15199816.8 dated Feb. 8, 2016.
Chang et al., "Elastase-inhibiting Activity in Scaling Skin Disorders", Short Reports, Acta Derm Venereol (Stockh), vol. 70, 1990, pp. 147-151.
Aikawa et al., "Clinical utility of the neutrophil elastase inhibitor sivelestat for the treatment of acute respiratory distress syndrome", Dove Press Journal: Therapeutics and Clinical Risk Management, vol. 10, Aug. 2014, pp. 621-629.
Almansa et al., "Critical COPD respiratory illness is linked to increased transcriptomic activity of neutrophil proteases genes", BMC Research Notes 2012, 5:401, 8 pages.
Kawabata et al., "ONO-5046, A Novel Inhibitor of Human Neutrophil Elastase" Biochemical and Biophysical Research Communications, vol. 177, No. 2, Jun. 1991, pp. 814-820.
Voegeli et al., "Increased stratum corneum serine protease activity in acute eczematous atopic skin", British Journal of Dermatology, vol. 161, 2009, pp. 70-77.
Brusselle et al., "Sputum Neutrophil Elastase as a Biomarker for Disease Activity in Bronchiectasis", American Journal of Respiratory and Critical Care Medicine: Editorials, vol. 195, No. 10, 2017, pp. 1289-1291.
Cantin et al., "Aerosolized Prolastin Suppresses Bacterial Proliferation in a Model of Chronic Pseudomonas aeruginosa Lung Infection", American Journal of Respiratory & Critical Care Medicine, vol. 160, 1999, pp. 1130-1135.
Carter et al., "Aa-Val$^{360}$: a marker of neutrophil elastase and COPD disease activity", European Respiratory Journal, vol. 41, No. 1, 2013, pp. 31-38.
Chalmers et al., "Neutrophil Elastase Activity Is Associated with Exacerbations and Lung Function Decline in Bronchiectasis", American Journal of Respiratory and Critical Care Medicine, vol. 195, No. 10, May 2017, pp. 1384-1393.
Chapman et al., "Intravenous augmentation treatment and lung density in severe al antitrypsin deficiency (RAPID): a randomised, double-blind, placebo-controlled trial", in Lancet: Articles [online] vol. 386, Jul. 2015, pp. 360-368, Retrieved from: www.thelancet.com.
Chua et al., "Mice Lacking Neutrophil Elastase Are Resistant to Bleomycin-Induced Pulmonary Fibrosis", The American Journal of Pathology: *Cardiovascular, Pulmonary and Renal Pathology*, vol. 170, No. 1, Jan. 2007, pp. 65-74 [online] <DOI: 10.2353/ajpath.2007.060352>.
Stockley, R., "Chronic Bronchitis: The Antiproteinase/Proteinase Balance and the Effect of Infection and Corticosteroids", Clinics in Chest Medicine: Inflammatory Disorders of the Airway, vol. 9, No. 4, Dec. 1988, pp. 643-656.
Silberer et al., "Fecal Leukocyte Proteins in Inflammatory Bowel Disease and Irritable Bowel Syndrome", Clin. Lab., vol. 51, 2005, pp. 117-126.
Elborn et al., "Efficacy, safety and effect on biomarkers of AZD9668 in cystic fibrosis", European Respiratory Journal, vol. 40, No. 4, 2012, pp. 969-976 [online] <DOI: 10.1183/09031936.00194611>.
Gaggar et al., "Matrix metalloprotease-9 dysregulation in lower airway secretions of cystic fibrosis patients", *Am J Phys—Lung Coil Mol Phys*, vol. 293, 2007, pp. L96-L104 [online], [retrieved on Jun. 19, 2017] Retrieved from the Internet: <URL: http://ajplung.physiology.org/> <DOI: 10.1152/ajplung.00492.2006>.
Gloro et al., "Protease-activated receptors potential therapeutic targets in irritable bowel syndrome'?", Expert Opinion on Therapeutic Targets, 9:5, 2005, pp. 1079-1095 [online], [retrieved on 2017-06-16] Retrieved from the Internet: <Url: http://dx.doi.org/10.1517/14728222.9.5.1079> <001: 10.1517/14728222.9.5.1079>.

(Continued)

*Primary Examiner* — Susanna Moore
(74) *Attorney, Agent, or Firm* — Oblon, McClelland, Maier & Neustadt, L.L.P.

(57) ABSTRACT

Triazolinone compounds of formula (I) defined herein exhibit human neutrophil elastase inhibitory properties and are useful for the therapy of diseases and conditions in which HNE is implicated.

14 Claims, No Drawings

(56) References Cited

OTHER PUBLICATIONS

Gregory et al., "Neutrophil elastase promotes myofibroblast differentiation in lung fibrosis", Journal of Leukocyte Biology, vol. 98, No. 2, 2015, pp. 143-152 [online] [retrieved Jun. 16m 2017] Retrieved from the Internet: <URL: www.jleukbio.org> <DOI: 10.1189/jlb.3HI1014-493R>.

Hagio et al., "Inhibition of neutrophil elastase reduces lung injury and bacterial count in hamsters", Pulmonary Pharmacology & Therapeutics, vol. 21, 2008, pp. 884-891 [online], <DOI: 10.1016/j.pupt.2008.10.002>.

Hirota et al., "Effects of the Neutrophil Elastase Inhibitor (ONO-6818) on Acetic Acid Induced Colitis in Syrian Hamsters", *Pharmacology: J. Vet. Med. Sci.*, vol. 66, No. 10, 2004, pp. 1223-1228.

Imokawa et al., "Acute respiratory failure due to pneumocystis pneumonia successfully treated with combined use of sivelestat sodium hydrate", Nihon Kokyuki Gakkai Zasshi, vol. 46, No. 6, Jun. 2008, pp. 461-465 (English Abstract only).

Janoff, "State of the Art: Elastases and Emphysema: Current Assessment of the Protease-Antiprotease Hypothesis", American Review of Respiratory Disease, vol. 132, 1985, pp. 417-433.

Janoff et al., "Possible Mechanisms of Emphysema in Smokers, Cigarette Smoke Condensate Suppresses Protease Inhibition in Vitro", American Review of Respiratory Disease, vol. 116, 1977, pp. 65-72.

Koga et al., "Inhibition of neutrophil elastase attenuates airway hyperresponsiveness and inflammation in a mouse model of secondary allergen challenge: neutrophil elastase inhibition attenuates allergic airway responses", Respiratory Research, vol. 14, No. 8, 2013, 13 pp. [online], Retrieved from the Internet: <URL: http://respiratory-research.com/content/14/1/8> <DOI: 10.1186/1465-9921-14-8>.

Kristensen et al., "Serologically assessed elastin degradation is related to force vital capacity in patients with IPF", European Resp Journal, 2014 (Abstract only).

Kuna et al., "AZD9668, a neutrophil elastase inhibitor, plus ongoing budesonide/formoterol in patients with COPD", Respiratory Medicine, vol. 106, 2012, pp. 531-539 [online], Retrieved from the Internet: <URL: www.sciencedirect.com> <DOI: 10.1016/j.rmed.2011.10.020>.

Macleod et al., "Neutrophil Elastase-mediated proteolysis activates the anti-inflammatory cytokine IL-36 Receptor antagonist", Scientific Reports, vol. 6, No. 24880, 2016, pp. 1-7 [online] Retrieved from the Internet: <URL: www.nature.com/scientificreports/> <DOI: 10.1038/srep24880>.

Yang et al., "$\alpha_1$—Antitrypsin Deficiency and Inflammatory Bowel Diseases", Mayo Clinic Proceedings, vol. 75, 2000, pp. 450-455.

Meyer-Hoffert et al., "Human Leukocyte Elastase Induces Keratinocyte Proliferation by Epidermal Growth Factor Receptor Activation", The Journal of Investigative Dermatology, vol. 123, Aug. 2004, pp. 338-345.

Narita et al., "A case of legionella pneumonia associated with acute respiratory distress syndrome (ARDS) and acute renal failure treated with methylprednisolone and sivelestat", Nihon Kokyuki Gakkai Zasshi, vol. 45, No. 5, May 2007, pp. 413-418 (English Abstract only).

Polverino et al., "The role of neutrophil elastase inhibitors in lung diseases", Chest: Official Publication of the American College of Chest Physicians, 2017 [online] Retrieved from the Internet: <DOI: 10.1016/j.chest.2017.03.056>.

Pott et al., "Alpha-1 antitrypsin reduces severity of Pseudomonas pneumonia in mice and inhibits epithelial barrier disruption and Pseudomonas invasion of respiratory epithelial cells", Frontiers in Public Health: Infectious Diseases, vol. 1, Article 19 Jun. 2013, pp. 1-13 [online] Retrieved from the Internet: <URL: http://www.frontiersin.org/> <DOI: 10.3389/fpubh.2013.00019>.

Sagel et al., "Airway Inflammation in Children with Cystic Fibrosis and Healthy Children Assessed by Sputum Induction", American Journal of Respiratory and Critical Care Medicine, vol. 164, 2001, pp. 1425-1431 [online] Retrieved from the Internet: <URL: www.atsjournals.org> <DOI: 10.1164/rccm2104075>.

Sagel et al., "Induced Sputum Matrix Metalloproteinase-9 Correlates with Lung Function and Airway Inflammation in Children with Cystic Fibrosis", Pediatric Pulmonology, vol. 39, 2005, pp. 224-232.

Sandhaus et al., "Neutrophil Elastase-Mediated Lung Disease", COPD: Journal of Chronic Obstructive Pulmonary Disease, vol. 10, S1, 2013, pp. 60-63 [online] [retrieved on Jun. 16, 2017] Retrieved from the Internet: <URL: http://dx.doi.org/10.3109/15412555.2013.764403> <DOI: 10.3109/15412555.2013.764403>.

Sftreide, K., "Proteinase-activated receptor 2 (PAR-2) in gastrointestinal and pancreatic pathophysiology, inflammation and neoplasia", Scandinavian Journal of Gastroenterology, vol. 43, No. 8, pp. 902-909 [online] [retrieved on Jun. 16, 2017] Retrieved from the Internet: <URL: http://dx.doi.org/10.1080/00365520801942141> <DOI: 10.1080/00365520801942141>.

Shapiro et al., "Neutrophil Elastase Contributes to Cigarette Smoke-Induced Emphysema in Mice", American Journal of Pathology, vol. 163, No. 6, Dec. 2003, pp. 2329-2335.

Shioya et al., "Neutrophil Elastase Inhibitor Suppresses IL-17 Based Inflammation of Murine Experimental Colitis", Fukushima J. Med. Sci.: *A New Therapeutic Approach for Ibd Patients*, vol. 60, No. 1, 2014, pp. 14-21.

Zhu et al., "Plasma Neutrophil Elastase and Elafn as Prognostic Biomarker for Acute Respiratory Distress Syndrome: A Multicenter Survival and Longitudinal Prospective Observation Study", Shock, 2017 [online] Retrieved from the Internet: <DOI: 10 1097/SHK.0000000000000845>.

Sly et al., "Risk Factors for Bronchiectasis in Children with Cystic Fibrosis", The New England Journal of Medicine, vol. 368, No. 21, May 2013, pp. 1963-1970 [online] [retrieved on Jun. 16, 2017] Retrieved from the Internet: <URL; nejm.org> <DOI: 10.1056/NEJMoa1301725>.

Salaga et al., "Inhibition of proteases as a novel theraputic strategy in the treatment of metabolic, inflammatory and functional diseases of the gastrointestinal tract", Drug Discovery Today, vol. 18, Nos. 15/16, Aug. 2013 [online], Retrieved from the Internet: <URL: www.drugdiscoverytoday.com> <DOI: 10.1016/j.drudis.2013.03.004>.

Sommerhoff et al, "Neutrophil Elastase and Cathepsin G Stimulate Secretion from Cultured Bovine Airway Gland Serous Cells", The Journal of Clinical Investigation, vol. 85, Issue 3, Mar. 1990, pp. 682-689 [online] [retrieved on Jun. 16, 2017] Retrieved from the Internet: <URL: http://www.jci.org> <Doi: 10.1172/JCI114492>.

Stevens et al., "AZD9668: Pharmacological Characterization of a Novel Oral Inhibitor of Neutrophil Elastase", Journal of Pharmacology and Experimental Therapeutics, vol. 339, No. 1, 2011, pp. 313-320 [online] [retrieved on Feb. 25, 2015] Retrieved from the Internet: <URL: http://jpet.aspetjournals.org/> <DOI: 10.1124/jpet.111.182139>.

Stockley et al., "Phase II Study of a Neutrophil Elastase Inhibitor (AZDQGBB) in Patients with Bronchiectasis", Respiratory Medicine, vol. 107, 2013, pp. 524-533 [online] Retrieved from the Internet: <URL: http://dx.doi.org/10.1016/j.rmed.2012.12.009>.

Taooka et al., "Effects of Neutrophil Elastase Inhibitor on Bleomycin-Induced Pulmonary Fibrosis in Mice", American Journal of Respiratory and Critical Care Medicine, vol. 155, 1997, pp. 260-265.

Takemasa et al., "A neutrophil elastase inhibitor prevents bleomyoineinduced pulmonary fibrosis in mice", European Respiratory Journal, vol. 40, No. 6, 2012, pp. 1475-1482.

Terui et al., "Production and Pharmacologic Modulation of the Granulocyte-Associated Allergic Responses to Ovalbumin in Murine Skin Models Induced by Injecting Ovalbuminispecific Th1 or Th2 Cells", The Journal of Investigative Dermatology, vol. 117, No. 2, Aug. 2001, pp. 236-243

Vergnolle, N., "Protease Inhibltion as new therapeutlc strategy for GI diseases", BMJ Journals: Gut, vol. 65, 2015, pp. 1215-1224 [online] [retrieved on Jun. 16, 2017]Retrieved from the Internet: <URL: http://gut.bmj.com> <DOI: 10.1136/gutjnl-2015-309147>.

Vignola et al., "Increased Levels of Elastase and $\alpha$-Antitrypsin in Sputum of Asthmatic Patients", American Journal of Respiratory and Critical Care Medicine, vol. 157, 1998, pp. 505-511.

(56) References Cited

OTHER PUBLICATIONS

Vogelmeier et al., "A Randomised, Placebo-Controlled, Dose-Finding Study Of AZD9668, An Oral Inhibitor of Neutrophil Elastase, in Patients with Chronic Obstructive Pulmonary Disease Treated with Tiotropium", Journal of Chronic Obstructive Pulmonary Disease, vol. 9, No. 2, 2012 pp. 111-120 [online] [retrieved on Jun. 16, 2017] Retrieved from the Internet: <URL: http:/fdx.doi.org/10.3109/154125552011.641803> <DOI: 10.3109/154125552011.641803>.

Westin et al., "The effect of immediate hypersensitivity reactions on the level of SLPI, granulocyte elastase, a1-antitwpsin, and albumin in nasal secretions, by the method of unilateral antigen challenge", Allergy, vol. 54, 1999, pp. 857-864.

Wiedow et al., "Lesional Elastase Activity in Psoriasis, Contact Dermatitis, and Atopic Dermatitis", The Journal of Investigative Dermatology, Vol, 99, No. 3, Sep. 1992, pp. 305-309.

Woods et al., "Aerosol Treatment with MNEI Suppresses Bacterial Proliferation in a Model of Chronic Pseudomonas aeruginosa Lung Infection", Pediatric Pulmonology, vol. 39, 2005, pp. 141-149.

Yanagihara et al., "Effects of Specific Neutrophil Elastase Inhibitor, Sivelestat Sodium Hydrate, in Murine Model of Severe Pneumococcal Pneumonia", Experimental Lung Research, vol. 33, No. 2, 2007, pp. 71-80 [online] [retrieved on Jun. 6, 2017] Retrieved from the Internet: <URL: http://dx.doi.org/10.1080/01902140701198500> <DOI: 10.1080/01902140701 198500>.

Yoshida et al., "Pathoblology of Cigarette Smoke-Induced Chronic Obstructive Pulmonary Disease", Physiological Reviews, vol. 87, 2007, pp. 1047-1082 [online] [retrieved on Jun. 16, 2017] Retrieved from the Internet: <URL: http://physrev.physiology.org/> <DOI: 10.1152/physrev.00048.2006>.

* cited by examiner

TRIAZOLINONE COMPOUNDS AS HNE INHIBITORS

CROSS REFERENCES TO RELATED APPLICATIONS

This application claims priority to European Patent Application No. 15199816.8 filed on Dec. 14, 2015, which is incorporated herein by reference in its entirety.

BACKGROUND OF THE INVENTION

Field of the Invention

This invention relates triazolinone derivatives having human neutrophil elastase inhibitory properties, and their use in therapy.

Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. in *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; and Churg, A. et al. *Am. J. Respir. Crit. Care Med.* 2003, 168, 199-207, both of which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as α1-antitrypsin ($α_1$-AT), secretory leukocyte protease inhibitor (SLPI) and pre-elafin leads to the various inflammatory disorders of COPD. Individuals that have a genetic deficiency of the protease inhibitor al-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far. In particular, WO2011/110858, WO2011/110859, WO 2014/095700, and WO 2015/091281, all of which are incorporated herein by reference in their entireties) describe pyrimidine derivatives having human neutrophil elastase inhibitory properties.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment.

SUMMARY OF THE INVENTION

Accordingly, it is one object of the present invention to provide novel compounds having human neutrophil elastase inhibitory properties.

It is another object of the present invention to provide novel triazolinone compounds having human neutrophil elastase inhibitory properties.

It is another object of the present invention to provided novel methods of treating certain disease and condition by administering such a compound.

These and other objects, which will become apparent during the following detailed description, have been achieved by the inventors' discovery of compound of formula (I):

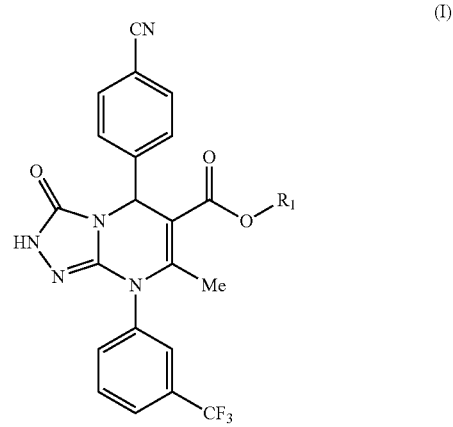

wherein
$R_1$ is —($C_1$-$C_6$)alkyl optionally substituted with one or more substituents selected from the group consisting of —$CO_2R_2$, —$SO_2R_2$, —NHC(O)$R_2$, and —$OR_2$;

R₂ is hydrogen or —(C₁-C₆)alkyl and
and pharmaceutically acceptable salts thereof.

The compounds of formula (I) can be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.

The compounds of the invention can be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) pharmaceutical compositions comprising a compound of the invention and a pharmaceutically acceptable carrier or excipient; and (ii) the treatment or prevention of a disease or condition in which HNE is implicated by administering a compound of the invention.

DETAILED DESCRIPTION OF THE PREFERRED EMBODIMENTS

The term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl, and n-hexyl.

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

The compounds of the invention which are acidic can form salts with bases such as alkali metal hydroxides, e.g. sodium and potassium hydroxides; alkaline earth metal hydroxides e.g. calcium, barium, and magnesium hydroxides; with organic bases e.g. N-methyl-D-glucamine, choline tris(hydroxymethyl)amino-methane, L-arginine, L-lysine, N-ethyl piperidine, dibenzylamine, and the like. The basic compounds which can form salts with inorganic acids, e.g. with hydrohalogen acids such as hydrochloric or hydrobromic acids, sulfuric acid, nitric acid or phosphoric acid, and the like, or with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids, and the like. The compounds having quaternary nitrogen can also form quaternary salts with a pharmaceutically acceptable counter-ion such as chloride, bromide, acetate, formate, phenylsulfonate, p-toluenesulfonate, succinate, hemi-succinate, naphthalenebis sulfonate, methanesulfonate, xinafoate, isethionate, and the like.

Where the compounds of the invention have at least one stereogenic center, they can exist as enantiomers. When the compounds according to the invention possess two or more stereogenic centers, they can additionally exist as diastereoisomers. It is to be understood that all such isomers and mixtures thereof in any proportion are encompassed within the scope of the present invention.

It will be apparent that compounds of general formula (I) contain at least one stereogenic center, namely represented by the carbon atom (1) with an asterisk below, and therefore exist as optical stereoisomers

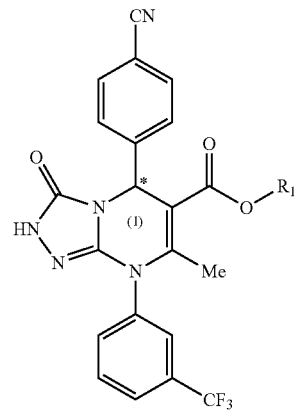

In one embodiment, the invention is directed to compounds of formula (I)', which are compounds of formula (I) as above defined where the absolute configuration of carbon (1) is that shown here below:

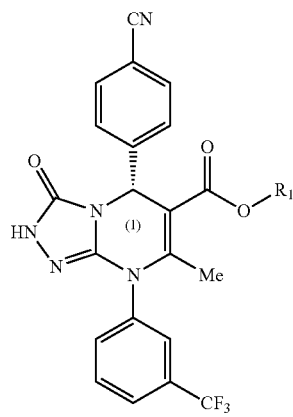

In another embodiment, the invention is directed to compounds of formula (I)", which are compounds of formula (I) as above defined where the absolute configuration of carbon (1) is that shown here below:

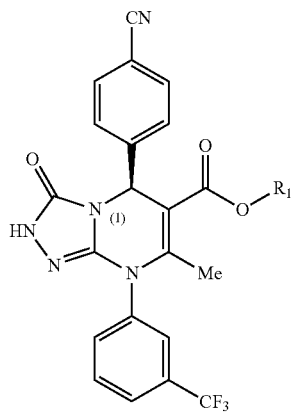

The absolute configuration for carbon (1) is assigned on the basis of Cahn-Ingold-Prelog nomenclature based on groups' priorities.

It is to be understood that all preferred groups or embodiments described here below for compounds of formula (I) may be combined among each other and apply as well to compounds of formula (I)' and (I)" mutatis mutandis.

In one embodiment for compounds of formula (I), (I)' or (I)", $R_1$ is —$(C_1\text{-}C_6)$alkyl substituted with one —$CO_2R_2$, wherein $R_2$ is hydrogen or —$(C_1\text{-}C_6)$alkyl.

In another embodiment for compounds of formula (I), (I)' or (I)", $R_1$ is —$(C_1\text{-}C_6)$alkyl substituted with one or more —$OR_2$, wherein $R_2$ is hydrogen or —$(C_1\text{-}C_6)$alkyl.

In another embodiment for compounds of formula (I), (I)' or (I)", $R_1$ is —$(C_1\text{-}C_6)$alkyl substituted with one or more —$SO_2R_2$, wherein $R_2$ is hydrogen or —$(C_1\text{-}C_6)$alkyl.

In another embodiment for compounds of formula (I), (I)' or (I)", $R_1$ is —$(C_1\text{-}C_6)$alkyl substituted with one or more —$NHC(O)R_2$, wherein $R_2$ is hydrogen or —$(C_1\text{-}C_6)$alkyl.

In another embodiment, the compound of the invention is selected in the group consisting of:

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-hydroxy-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methanesulfonyl-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxy-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxycarbonyl-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-carboxy-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-ethyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-acetylamino-propyl ester (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-propyl ester;

(R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2,3-dihydroxy-propyl ester.

The therapeutic utility of the present compounds is pertinent to any disease that is known to be at least partially mediated by the action of human neutrophil elastase. For example, the present compounds can be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds can be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K); (15) anti-retroviral agents such as ribavirin, zanamivir or laninamivir; (16) PPAR-γ agonists such as pioglitazone and rosiglitazone.

In one aspect, the present invention concerns the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the present invention concerns the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacaterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients can be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it can be necessary to use dosages outside these limits in some cases.

Another aspect of the present invention concerns pharmaceutical compositions which comprise a compound of the invention and a pharmaceutically acceptable carrier. The pharmaceutical compositions of the invention comprise a compound of the invention as an active ingredient or a pharmaceutically acceptable salt thereof, and can also contain a pharmaceutically acceptable carrier and optionally other therapeutic ingredients.

Any suitable route of administration can be employed for providing a mammal, especially a human, with an effective dosage of a compound of the invention. In therapeutic use, the active compound can be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and can include carriers and/or diluents that are known for use in such compositions. The composition can contain 0.01 to 99% by weight of active compound. Preferably, a unit dose comprises the active compound in an amount of 1 g to 10 mg.

The most suitable dosage level can be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They can be prepared by a variety of techniques, including spray-drying, freeze-drying and micronization.

By way of example, a composition of the invention can be prepared as a suspension for delivery from a nebuliser or as an aerosol in a liquid propellant, for example for use in a pressurized metered dose inhaler (PMDI). Propellants suitable for use in a PMDI are known and include CFC-12, HFA-134a, HFA-227, HCFC-22 (CCl2F2) and HFA-152 (CH4F2 and isobutane).

In a preferred embodiment, a composition is in dry powder form, for delivery using a dry powder inhaler (DPI). Many types of DPI are known.

Microparticles for delivery by administration can be formulated with excipients that aid delivery and release. For example, in a dry powder formulation, microparticles can be formulated with large carrier particles that aid flow from the DPI into the lung. Suitable carrier particles are known, and include lactose particles; they can have a mass median aerodynamic diameter of greater than 90 μm.

In the case of an aerosol-based formulation, a preferred composition is:

| Compound of the invention | 24 mg/canister |
|---|---|
| Lecithin, NF Liq. Conc. | 1.2 mg/canister |
| Trichlorofluoromethane, NF | 4.025 g/canister |
| Dichlorodifluoromethane, NF | 12.15 g/canister. |

The compounds of the invention can be used in combination with other drugs that are used in the treatment/prevention/suppression or amelioration of the diseases or conditions for which present compounds are useful. Such other drugs can be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients, in addition to a compound of the invention.

The agents of the invention can be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds can be dosed as described depending on the inhaler system used. In addition to the active compounds, the administration forms can additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0 505 321, which is incorporated herein by reference in its entirety).

Methods of Synthesis

In one aspect of the present invention, a process for the preparation of compounds of the invention (Ib)' is provided according to the general synthetic routes reported in Scheme A here below. Compounds (Ib)' are compounds of formula (I)' as above defined where the absolute configuration of carbon (1) is that shown here below, i.e. compounds of formula (I)' wherein $R_1$ is —$(C_1$-$C_6)$alkyl optionally substituted with one or more substituents selected from the group consisting of —$CO_2R_2$, —$SO_2R_2$, —$NHC(O)R_2$, and —$OR_2$ Scheme A

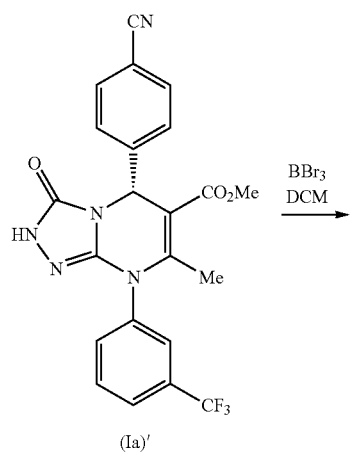

(Ia)'

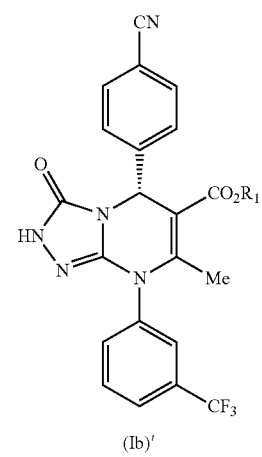

The compounds of formula (II) may be prepared from compounds of formula (Ia)' (prepared according to WO2013/037809 A1, which is incorporated herein by reference in its entirety, Example 7) by treating with a strong Lewis acid such as boron tribromide in a solvent such as DCM at a temperature of from −78° C. to RT followed by quench with water or methanol. Compounds of formula (II) may be converted into Compounds of formula (Ib)' by reaction with an alkyl halide of formula R1X such as an alkyl iodide in a solvent such as MeCN in the presence of a base such as 1M aqueous NaOH at RT or by reaction with an alcohol R1OH in the presence of a coupling agent such as HATU in a solvent such as DMF in the presence of a base such as DIPEA at a temperature.

The compounds of formula (Ia)' which are compounds of formula (I)' as defined above where the absolute configuration of carbon (1) is that shown here below may be prepared according to Scheme B below.

Scheme B

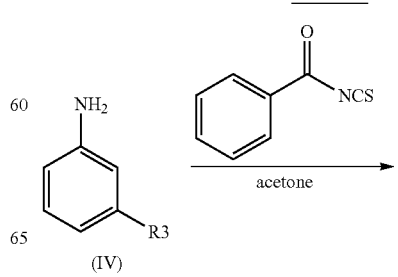

(IV)

-continued

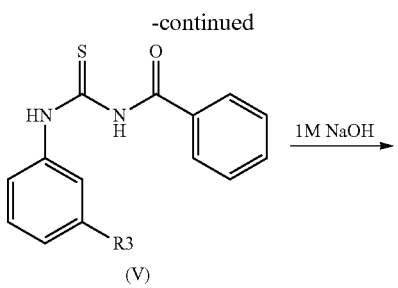

(V)

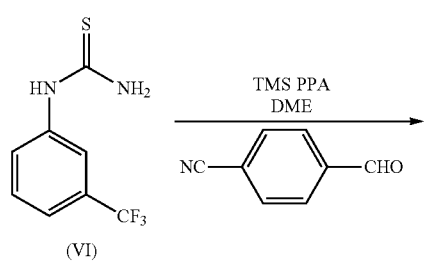

(VI)

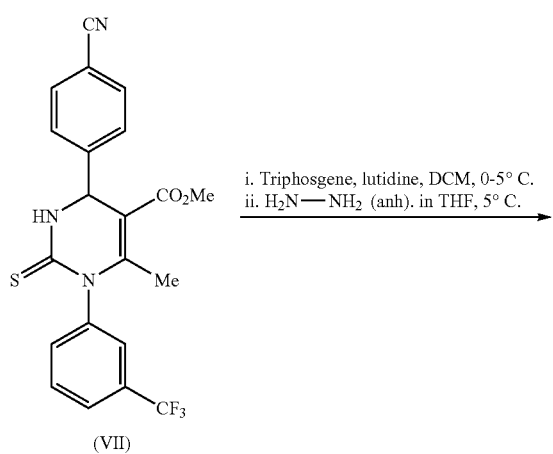

(VII)

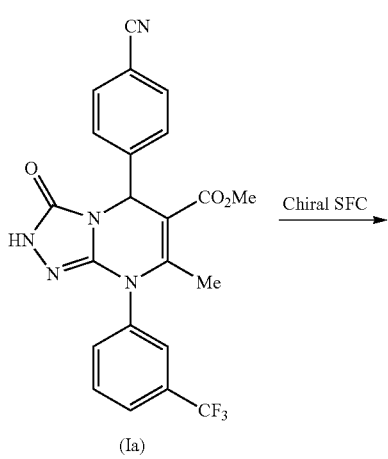

(Ia)

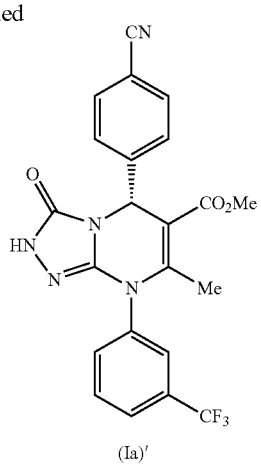

(Ia)'

The compounds of formula (V) may be prepared from compounds of formula (IV) by reacting with benzoyl isothiocyanate in a solvent such as acetone at a temperature of reflux. The compounds of formula (V) may be converted into compounds of formula (VI) by heating with 1M aqueous NaOH at 80° C. Compounds of formula (VI) may be reacted with 4-formyl-benzonitrile and an ethyl acetoacetate in the presence of an acid such as TMS-polyphosphate or polyphosphoric acid in a solvent such as THF at a temperature from RT to reflux to give compounds of formula (VII). The compounds of formula (Ia), which are compounds of formula (I) as above defined may be obtained from compounds of formula (VII) by reacting with a chlorocarbonyl-containing/releasing compound such as phosgene or triphosgene and anhydrous hydrazine in the presence of a base such as 2,6-lutidine in a solvent such as dichloromethane at a temperature of −5 to 5° C. to give compounds of formula (Ia). The compounds of formula (Ia)', which are compounds of formula (Ia) as above defined and wherein the absolute configuration of carbon (1) is that shown in Scheme B, may be obtained from compounds of formula (Ia) using chiral Supercritical Fluid chromatography (SFC).

Other features of the invention will become apparent in the course of the following descriptions of exemplary embodiments which are given for illustration of the invention and are not intended to be limiting thereof.

EXAMPLES

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled, the organic fraction removed by evaporation, and the remaining aqueous fraction lyophilized, to give the final product. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40 to 250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using the Autonom 2000 feature in MDL ISIS™/Draw 2.5 SP2 software.

Analytical LC-MS Conditions

LC-MS Method 1

The Waters ZQ quadrupole mass spectrometer with a C18-reverse-phase column (30×4.6 mm Phenomenex Luna 3 m particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 µl/min split to the ESI source with in-line HP1100 PDA detector)

MS ionization method—Electrospray (positive and negative ion)

LC-MS Method 2

Waters Micromass ZMD quadrupole mass spectrometer with a C18-reverse-phase column (30×4.6 mm Phenomenex Luna 3 m particle size), elution with A: water+0.1% formic acid; B: MeCN+0.1% formic acid. Gradient:

| Gradient - Time | flow(mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 µl split to MS with in-line UV detector)

MS ionization method—Electrospray (positive and negative ion)

LC-MS Method 3

Waters Micromass ZQ2000 mass spectrometer with a C18-reverse-phase column (100×2.1 mm Acquity BEH with 1.7 m particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 m particle size) column was used.

Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

Abbreviations used in the experimental section:
DCM Dichloromethane
DIPEA Di-isopropylethylamine
DMF N,N-dimethylformamide
DMSO Dimethylsulphoxide
EtOAc Ethyl acetate
HATU (1-[Bis(dimethylamino)methylene]-1H-1,2,3-triazolo[4,5-b]pyridinium 3-oxid hexafluorophosphate)
IMS Industrial methylated spirits
LC-MS Liquid chromatography-mass spectrometry
MeCN Acetonitrile
Rt Retention time
RT Room temperature
THF Tetrahydrofuran
TMS PPE Polyphosphoric acid trimethylsilyl ester In the following procedures, some of the starting materials are identified through an "Intermediate" or "Example" number. This is provided merely for assistance to the skilled chemist. The starting material may not necessarily have been prepared from the batch referred to.

Intermediate (A). (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid

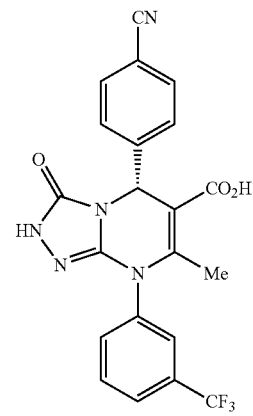 [SMILES: CC1=C(C(=O)O)[C@@H](c2ccc(C#N)cc2)n2c(n[nH]c2=O)N1c1cccc(C(F)(F)F)c1]

A solution of (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester (1.825 g, 4.0 mmol) (prepared according to WO2013/

037809 A1, which is incorporated herein by reference in its entirety, Example 7) in DCM (40 mL) under a nitrogen atmosphere was chilled to −50° C. and treated with boron tribromide (20 mL of a 1.0M solution in DCM, 20 mmol) at such a rate that the internal temperature remained below −40° C. The resultant suspension was stirred whilst warming slowly to −10° C. over 1.5 hours then without external cooling for a further 1.5 h. The mixture was cooled back to 0° C. and treated cautiously with water (5 mL). The resultant mixture was partitioned between water (50 mL) and DCM (50 mL). The aqueous phase was extracted with EtOAc (2×50 mL). The combined organic phase was extracted with 3×100 mL portions of a solution of saturated sodium carbonate (5 mL) in water (95 mL). The combined aqueous extract was acidified (1M HCl) and extracted with EtOAc (3×50 mL). The combined organic phase was dried ($Na_2SO_4$) and concentrated in vacuo to afford the title compound (1.35 g).

LC-MS (Method 2): Rt=3.02 min, [M+H]$^+$ 442.1

Intermediate (B). (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-(tert-butyl-dimethyl-silanyloxy)-propyl ester

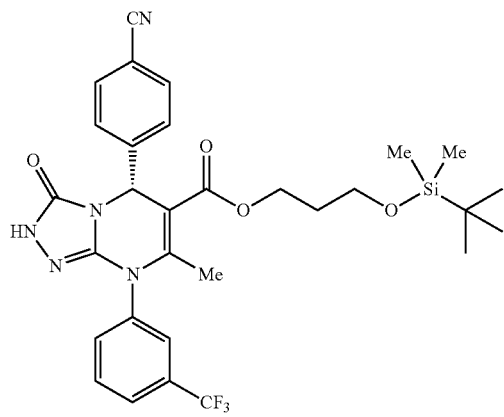 [SMILES: CC1=C(C(=O)OCCCO[Si](C)(C)C(C)(C)C)[C@@H](c2ccc(C#N)cc2)n2c(n[nH]c2=O)N1c1cccc(C(F)(F)F)c1]

(3-Bromo-propoxy)-tert-butyl-dimethyl-silane (1.0 mL, 4.3 mmol) was added to a solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (0.60 g, 1.36 mmol) in MeCN (10 mL) and 1M NaOH (1.40 mL, 1.4 mmol). The mixture was heated to 70° C. for 26 hours. The cold mixture was partitioned between EtOAc (15 mL) and water (15 mL). The aqueous phase was extracted with EtOAc (15 mL). The combined organic phase was dried ($Na_2SO_4$) and concentrated in vacuo. The residue was purified by chromatography on a 10 g Si II SPE cartridge eluting with 0-50% EtOAc in DCM in 10% increments to afford the title compound (0.50 g).

LC-MS (Method 1): Rt=4.42 min, [M+H]$^+$ 614.4

Example 1. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-hydroxy-propyl ester

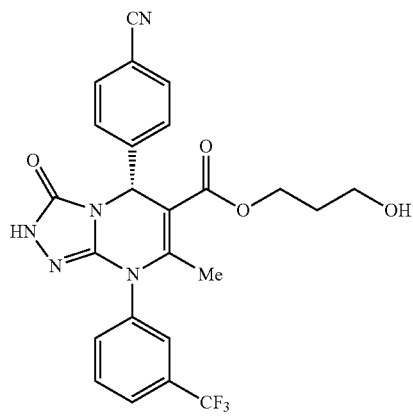 [SMILES: CC1=C(C(=O)OCCCO)[C@@H](c2ccc(C#N)cc2)n2c(n[nH]c2=O)N1c1cccc(C(F)(F)F)c1]

Concentrated HCl (0.20 mL) was added to a solution of Intermediate (B) (R)-5-(4-cyano-phenyl)-7-methyl-3-oxo-8-(3-trifluoromethyl-phenyl)-2,3,5,8-tetrahydro[1,2,4]triazolo-[4,3-a]pyrimidine-6-carboxylic acid 3-(tert-butyl-dimethyl-silanyloxy)-propyl ester (0.61 g, 1.0 mmol) in IMS (20 mL). The mixture was stirred for 1 hour then filtered through a 20 g flash NH2 cartridge washing with IMS (50 mL). The combined filtrate was concentrated in vacuo. The residue was purified by flash chromatography on a 10 g silica spe column loading with DCM and eluting with 1:1 DCM:EtOAc, EtOAc then 10% MeOH in EtOAc to afford the title compound (0.46 g).

LCMS (Method 3): Rt=3.94 min, [M+H]$^+$ 500.1

$^1$H NMR (400 MHz, $CDCl_3$) δ 8.48 (1H, s), 7.81 (1H, d J=7.9 Hz), 7.75-7.65 (3H, m), 7.63-7.53 (4H, m), 6.14 (1H, s), 4.25-4.18 (2H, m), 3.55-3.41 (2H, m), 2.30 (3H, s), 1.81-1.67 (3H, m).

Example 2. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methanesulfonyl-propyl ester

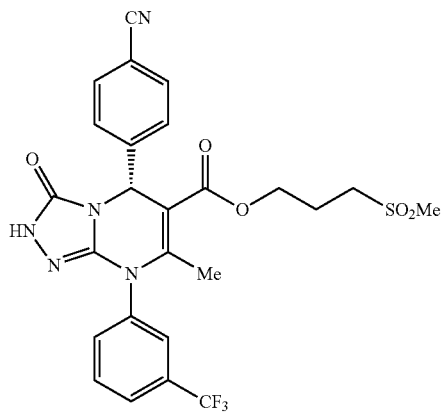

1-Bromo-3-methanesulfonyl-propane (201 mg, 1.0 mmol) was added to a solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (120 mg, 0.27 mmol) in MeCN (2.0 mL) and 1M NaOH (0.25 mL, 0.25 mmol). The mixture was heated to 70° C. for 16 hours. The cold mixture was partitioned between EtOAc (10 mL) and water (10 mL). The aqueous phase was washed with EtOAc (10 mL). The combined organic phase was dried (Na₂SO₄) and concentrated in vacuo. The residue was purified by flash column chromatography using a 2 g Si II SPE column loading with DCM and eluting with DCM 10%, 20%, 30%, 40% and then 50% EtOAc in DCM to afford the title compound (71 mg).

LCMS (Method 3): Rt=4.01 min, [M+H]⁺ 562.1

¹H NMR (CDCl₃) δ 8.64 (1H, s), 7.81 (1H, d J=7.9 Hz), 7.75-7.67 (3H, m), 7.63-7.53 (4H, m), 6.11 (1H, s), 4.19 (2H, t J=6.1 Hz), 2.87 (3H, s), 2.83-2.73 (2H, m), 2.31 (3H, s), 2.15-2.05 (2H, m).

Example 3. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxy-propyl ester

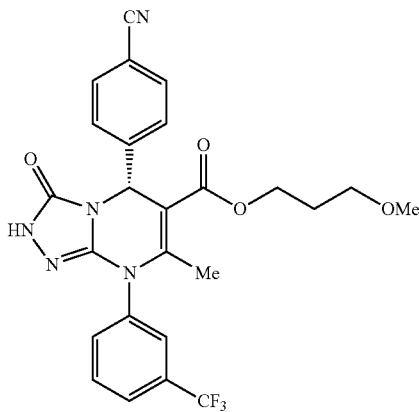 [SMILES: COCCCOC(=O)C1=C(C)N(c2cccc(C(F)(F)F)c2)c2n[nH]c(=O)n2[C@@H]1c1ccc(C#N)cc1]

1-Bromo-3-methoxy-propane (150 mg, 1.0 mmol) was added to a solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (120 mg, 0.27 mmol) in MeCN (2.0 mL) and 1M NaOH (0.25 mL, 0.25 mmol). The mixture was heated to 70° C. for 24 hours. The cold mixture was partitioned between EtOAc (10 mL) and a mixture of water (9 mL) and saturated sodium hydrogen carbonate (1 mL). The aqueous phase was washed with EtOAc (10 mL). The combined organic phase was dried (Na₂SO₄) and concentrated in vacuo. The residue was purified by flash column chromatography using a 2 g Si II SPE column loading with DCM and eluting with DCM 10%, 20%, 30%, 40% then 50% EtOAc in DCM and then EtOAc to afford the title compound (85 mg).

LCMS (Method 3): Rt=4.50 min, [M+H]⁺514.1

¹H NMR (400 MHz, CDCl3) δ 8.41 (1H, s), 7.80 (1H, d J=7.9 Hz), 7.74-7.66 (3H, m), 7.62-7.53 (4H, m), 6.14 (1H, s), 4.18-4-08 (2H, m), 3.30-3.20 (5H, m), 2.30 (3H, s), 1.82-1.74 (2H, m).

Example 4. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxycarbonyl-propyl ester

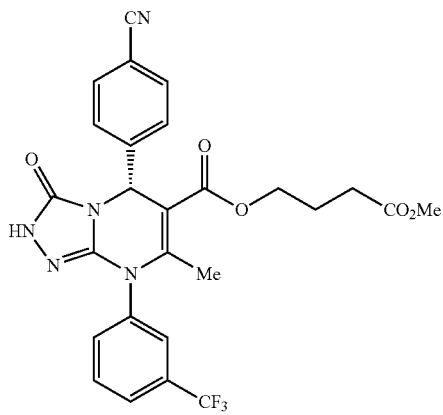 [SMILES: COC(=O)CCCOC(=O)C1=C(C)N(c2cccc(C(F)(F)F)c2)c2n[nH]c(=O)n2[C@@H]1c1ccc(C#N)cc1]

4-Bromo-butyric acid methyl ester (295 mg, 1.63 mmol) was added to a solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (290 mg, 0.65 mmol) in MeCN (5.0 mL) and 1M NaOH (0.64 mL, 0.64 mmol). The mixture was heated to 70° C. for 15 hours. The cold mixture was partitioned between EtOAc (10 mL) and a mixture of water (10 mL) and saturated sodium hydrogen carbonate (2 mL). The organic phase was washed with water (10 mL) dried (Na₂SO₄) and concentrated in vacuo. The residue was purified by flash column chromatography using a 2 g Si II SPE column loading with DCM and eluting with DCM 10%, 20%, 30%, 40% then 50% EtOAc in DCM and then EtOAc to afford the title compound (220 mg).

LC-MS (Method 3): Rt=4.51 min, [M+H]⁺ 542.2

¹H NMR (400 MHz, CDCl3); δ 8.38 (1H, s), 7.81 (1H, d J=7.9 Hz), 7.74-7.66 (3H, m), 7.63-7.53 (4H, m), 6.11 (1H, s), 4.12-4.04 (2H, m), 3.69 (3H, s), 2.30 (3H, s), 2.18-2.04 (2H, m), 1.88-1.80 (2H, m).

Example 5. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-carboxy-propyl ester

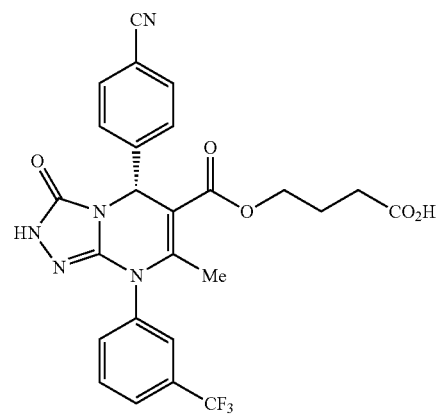 [SMILES: CC1=C(C(=O)OCCCC(=O)O)[C@@H](c2ccc(C#N)cc2)n2c(n[nH]c2=O)N1c1cccc(C(F)(F)F)c1]

A solution of Example 4 (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxycarbonyl-propyl ester (220 mg, 0.4 mmol) and lithium hydroxide hydrate (20 mg 0.47 mmol) in THF (5.0 ml) and water (1.0 mL) was stirred at ambient temperature for 16 hours then at 45° C. for a further 3 hours. The cold mixture was diluted with EtOAc (15 mL) then extracted with a mixture of water (10 mL) and saturated sodium hydrogen carbonate (2.0 mL). The organic phase was washed with water (2×5 mL). The combined aqueous phase was acidified with 1M HCl and extracted with EtOAc (3×10 ml). The organic phases were combined, dried (Na$_2$SO$_4$) and concentrated in vacuo. The residue obtained was freeze-dried from MeCN/water to afford the title compound as a white solid (75 mg).

LC-MS (Method 3): Rt=4.04 min, [M+H]$^+$ 528.1

$^1$H NMR (400 MHz, DMSO) δ 12.05 (1H, br s), 11.20 (1H, s), 8.05 (1H, s), 7.90-7.73 (5H, m), 7.66 (2H, d J=8.3 Hz), 5.90 (1H, s), 3.99-3.88 (2H, m), 2.15 (3H, s), 2.06-1.99 (2H, m), 1.70-1.61 (2H, m).

Intermediate (C). (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-(tert-butyl-dimethyl-silanyloxy)-ethyl ester

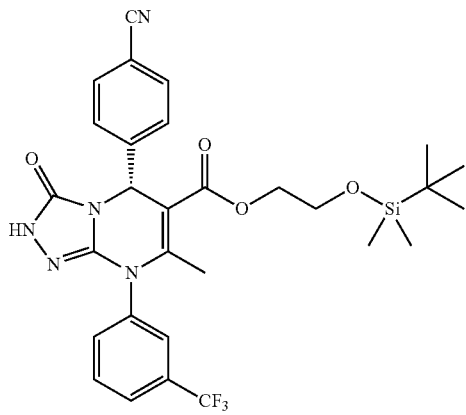 [SMILES: CC1=C(C(=O)OCCO[Si](C)(C)C(C)(C)C)[C@@H](c2ccc(C#N)cc2)n2c(n[nH]c2=O)N1c1cccc(C(F)(F)F)c1]

(2-Bromo-ethoxy)-tert-butyl-dimethyl-silane (143 mg, 0.6 mmol) was added to a solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (90 mg, 0.20 mmol) in MeCN (2.0 mL) and 1M NaOH (0.20 mL, 0.20 mmol). The mixture was heated at 70° C. for 24 hours. A second aliquot of (2-bromo-ethoxy)-tert-butyl-dimethyl-silane was added and the mixture was heated to 70° C. for a further 24 hours. The cold mixture was diluted with water (10 mL) and extracted with EtOAc (2×10 mL). The combined organic phase was dried (Na$_2$SO$_4$) and concentrated in vacuo. The residue was purified by flash column chromatography using a 5 g Si II SPE column loading with DCM and eluting with DCM 10%, 20%, 30%, 40% and then 50% EtOAc in DCM to afford the title compound (70 mg).

LC-MS (Method 1): Rt=4.34 min, [M+H]$^+$ 600.1

Example 6. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-ethyl ester

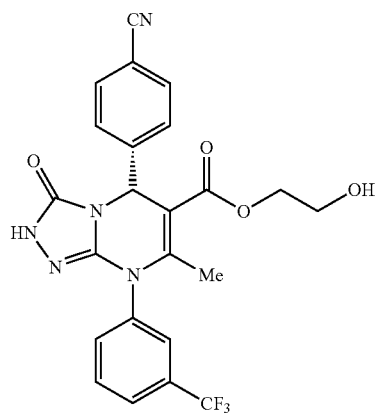

Concentrated HCl (0.05 mL) was added to a solution of Intermediate (C) (R)-5-(4-cyano-phenyl)-7-methyl-3-oxo-8-(3-trifluoromethyl-phenyl)-2,3,5,8-tetrahydro-[1,2,4]triazolo-[4,3-a]pyrimidine-6-carboxylic acid 2-(tert-butyl-dimethyl-silanyloxy)-ethyl ester (0.61 g, 1.0 mmol) in IMS (5.0 mL). The mixture was stirred for 16 hours then filtered through a 2 g flash NH2 cartridge washing with IMS (10 mL). The combined filtrate was concentrated in vacuo. The residue was purified by flash chromatography on a 2 g silica Si II SPE column loading with DCM and eluting with 1:1 DCM:EtOAc and then EtOAc to afford the title compound (35 mg).

LC-MS (Method 3): Rt=3.88 min, [M+H]$^+$ 486.2

$^1$H NMR (400 MHz; CDCl$_3$) δ 8.85 (1H, s), 7.80 (1H, d J=7.9 Hz), 7.72 (1H, t J=7.9 Hz), 7.66 (2H, d J=8.4 Hz), 7.63-7.59 (3H, m), 7.56 (1H, d J=7.9 Hz), 6.34 (1H, s), 4.29-4.22 (1H, m), 4.12-4.05 (1H, m), 3.79-3.71 (2H, m), 2.53 (1H, t J=5.2 Hz) 2.30 (3H, s).

Example 7. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-acetylamino-propyl ester

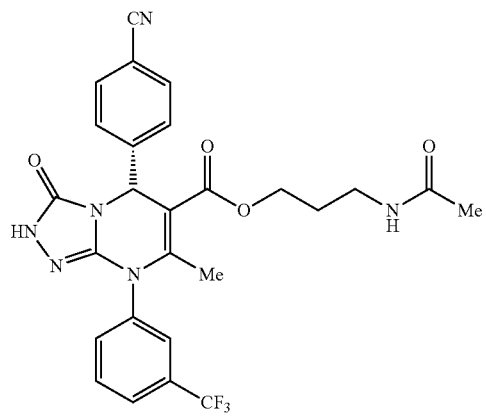

A solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (88 mg, 0.2 mmol) in DMF (3 mL) and DIPEA (52 mg, 0.4 mmol) was treated with HATU (152 mg, 0.4 mmol). The mixture was stirred for 15 minutes then N-(3-hydroxy-propyl)-acetamide (130 mg, 1.1 mmol) was added. The mixture was stirred for 6 hours then allowed to stand for 2 days. The mixture was treated with 30% aqueous ammonia (0.25 mL) and stirred for 2 h. Water (20 mL) was added and the mixture was extracted with EtOAc (2×10 mL). The combined organic phase was washed with saturated brine, dried (Na$_2$SO$_4$) and concentrated in vacuo. The residue was purified by flash chromatography using a 2 g Si II silica cartridge loaded with DCM and eluted with EtOAc then 10% MeOH in EtOAc to afford the title compound (68 mg).

LC-MS (Method 3): Rt=3.86 min, [M+H]$^+$ 541.3

$^1$H NMR (400 MHz, CDCl$_3$) δ 8.52 (1H, s), 7.80 (1H, d J=7.9 Hz), 7.75-7.66 (3H, m), 7.62-7.54 (4H, m), 6.13 (1H, s), 5.55 (1H, br s), 4.10 (2H, t J=6.1 Hz), 3.20-3.00 (2H, m), 2.31 (3H, s), 1.96 (3H, s), 1.78-1.65 (2H, m).

Example 8. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-propyl ester

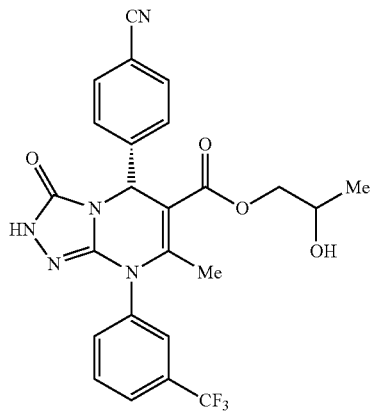

A mixture of (±)-propylene oxide (83 mg, 1.56 mmol), Intermediate (A) (R)-5-(4-cyano-phenyl)-7-methyl-3-oxo-8-(3-trifluoromethyl-phenyl)-2,3,5,8-tetrahydro[1,2,4]triazolo[4,3-a]pyrimidine-6-carboxylic acid (130 mg, 0.29 mmol), MeCN (2.0 mL), and 1M NaOH (0.20 mL, 0.20 mmol) was heated to 70° C. for 24 hours. The cold mixture was diluted with water (10 mL) and extracted with EtOAc (10 mL). The organic phase was washed with a mixture of water (9 mL) and saturated sodium hydrogen carbonate solution (1 mL). The combined aqueous phase was back washed with EtOAc (10 mL). The combined organic phase was dried (Na$_2$SO$_4$) and concentrated in vacuo. The residue was purified by flash column chromatography using a 2 g Si II SPE column loading with DCM and eluting with DCM 10%, 20%, 30%, 40% then 50% EtOAc in DCM and then EtOAc. The crude product thus obtained was further purified on a 0.5 g Si II silica cartridge eluting with 1:1 DCM:EtOAc to afford the title compound (12 mg) as a 55:45 mixture of isomers.

LC-MS (Method 3): Rt=4.07 and 4.09 min, [M+H]$^+$ 500.2

$^1$H NMR (400 MHz, CDCl$_3$) δ 8.53 (s) and 8.51 (s) (together 1H), 7.81 (1H d J=7.9 Hz), 7.75-7.53 (7H, m), 6.27 (s) and 6.25 (s) (together 1H), 4.10 (d J=9.0 Hz of d J=2.7 Hz) and 4.03 (d J=11.2 of d J=2.9 Hz) (together 1H), 3.98-3.85 (2H, m), 2.32 (3H, s), 2.12 (br s) and 1.90 (br s) (together 1H), 1.11 (d J=4.2 Hz) and 1.10 (d J=4.2 Hz) (together 3H).

Intermediate (D). (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2,2-dimethyl-[1,3]dioxolan-4-ylmethyl ester

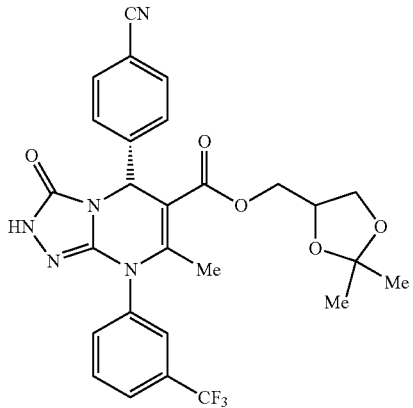

A solution of Intermediate (A) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid (88 mg, 0.2 mmol) in DMF (3 mL) and DIPEA (52 mg, 0.4 mmol) was treated with HATU (152 mg, 0.4 mmol). The mixture was stirred for 15 minutes then (±)-2,2-dimethyl-1,3-dioxolane-4-methanol (132 mg, 1 mmol) was added. The mixture was stirred for 7 hours and then allowed to stand overnight. The mixture was treated with 30% aqueous ammonia (0.25 mL) and stirred for 2 h. Water (15 mL) was added and the mixture was extracted with EtOAc (1×20 mL then 1×10 mL). The combined organic phase was washed with saturated brine, dried (Na$_2$SO$_4$) and concentrated in vacuo to afford the product (90 mg) which was used without further purification.

LC-MS (Method 1): Rt=3.47 min, [M+H]$^+$ 556.1

Example 9. (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2,3-dihydroxy-propyl ester

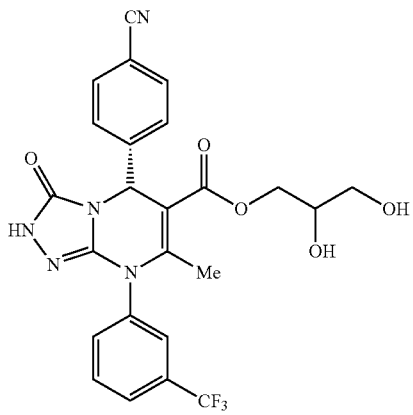

A solution of Intermediate (D) (R)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2,2-dimethyl-[1,3]dioxolan-4-ylmethyl ester (90 mg, 0.16 mmol) in IMS (2.0 mL) and 1M HCl (2.0 mL) was stirred at ambient temperature for 4 hours. The mixture was filtered through a 2 g flash NH2 cartridge, rinsing with MeCN (10 mL). The filtrate was concentrated in vacuo. The residue was reconcentrated twice from MeCN to remove water then purified by flash chromatography on a 2 g Si II SPE column loading in DCM and eluting with 1:1 DCM:EtOAc, EtOAc, 2% then 5% MeOH in EtOAc. Solvent residue was removed by freeze drying from MeCN/water to afford the title compound (40 mg) as a mixture of isomers.

LC-MS (Method 3): Rt=3.59 min, [M+H]$^+$ 516.2

$^1$H NMR (400 MHz, DMSO) δ 11.26 and 11.25 (together overlapping singlets, 1H), 8.10 (1H, s), 7.94-7.88 (2H, m), 7.86-7.78 (3H, m), 7.73-7.67 (2H, m), 6.04 (s) and 6.01 (s) (together 1H), 5.04 (d J=4.9 Hz) and 4.93 (d J=5.3 Hz) (together 1H), 4.62 (1H, t J=5.5 Hz), 4.11 (d J=11.3 of d J=4.0 Hz) with 3.75 (d J=11.1 Hz of d J=6.2 Hz) (together 1H), 3.91 (1H, d J=5.3 Hz), 3.64-3.56 (1H, m), 3.35-3.20 (integration unclear partially obscured by the water peak, m), 2.17 (3H s).

Biological Assay

The compounds of this invention were tested for potency in a human neutrophil elastase (HNE) enzyme activity assay.

HNE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency (IC$_{50}$) was determined. The compounds were tested in at least two separate experiments. IC$_{50}$ values (HNE enzyme inhibition) for all the Examples are <1 nM.

Neutrophil Enzyme Assay

Assays were performed in 96-well plates in a total assay volume of 100 μL. The final concentration of activated Rat or Human Neutrophils set to give the same signal window of elastase enzyme at 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl$_2$, 0.0005% brij-35, pH 7.5). The neutrophil reaction was started by addition of activated neutrophils and incubated at 37° C. for 30 minutes. After incubation, the reaction was stopped by addition of soybean trypsin inhibitor (Sigma T9003) at a final concentration of 50 μg/well. Fluorescence was measured using a Perkin Elmer fluorescence plate reader using 380 nm excitation and 460 nm emission wavelengths.

A dose response to each compound was performed and the effect of the compound in each experiment was expressed as a percentage inhibition of the control enzyme fluorescence. Dose response curves were plotted and compound potency (IC$_{50}$) was determined. The compounds were tested in at least two separate experiments against Rat and Human activated Neutrophils.

IC$_{50}$ values (Human protease inhibition) for all the Examples are <1 nM.

IC$_{50}$ values (Rat protease inhibition) for all the Examples are <10 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

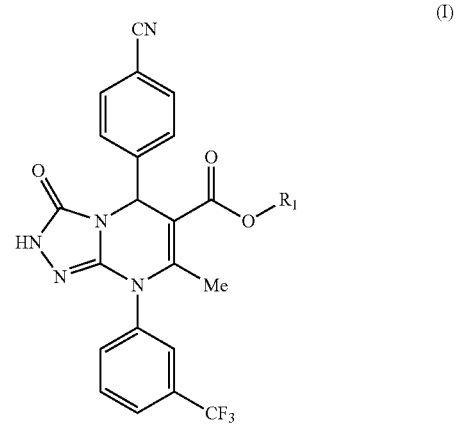

wherein

R$_1$ is —(C$_1$-C$_6$)alkyl, substituted with one or more substituents selected from the group consisting of —CO$_2$R$_2$, —SO$_2$R$_2$, —NHC(O)R$_2$, and —OR$_2$;

R$_2$ is hydrogen or —(C$_1$-C$_6$)alkyl, or a pharmaceutically acceptable salt thereof.

2. A compound or pharmaceutically acceptable salt according to claim 1, wherein R$_1$ is —(C$_1$-C$_6$)alkyl substituted with one —CO$_2$R$_2$ and R$_2$ is hydrogen or —(C$_1$-C$_6$)alkyl.

3. A compound or pharmaceutically acceptable salt according to claim 1, wherein R$_1$ is —(C$_1$-C$_6$)alkyl substituted with one or more —OR$_2$ and R$_2$ is hydrogen or —(C$_1$-C$_6$)alkyl.

4. A compound or pharmaceutically acceptable salt according to claim 1, wherein R$_1$ is —(C$_1$-C$_6$)alkyl substituted with one or more —SO$_2$R$_2$ and R$_2$ is hydrogen or —(C$_1$-C$_6$)alkyl.

5. A compound or pharmaceutically acceptable salt according to claim 1, wherein $R_1$ is —$(C_1$-$C_6)$alkyl substituted with one or more —NHC(O)$R_2$, wherein $R_2$ is hydrogen or —$(C_1$-$C_6)$alkyl.

6. A compound or pharmaceutically acceptable salt, which is a compound selected from the group consisting of
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-hydroxy-propyl ester;
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methanesulfonyl-propyl ester;
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-methoxy-propyl ester;
- (R)-5-(4-Cyano-phenyl)-7-methyl-3-oxo-8-(3 trifluoromethyl-phenyl)-2,3,5,8-tetrahydro-[1,2,4]triazolo[4,3-a]pyrimidine-6-carboxylic acid 3-methoxycarbonyl-propyl ester;
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-carboxy-propyl ester;
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-ethyl ester;
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-acetylamino-propyl ester
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-hydroxy-propyl ester; and
- (R)-5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2,3-dihydroxy-propyl ester, or a pharmaceutically acceptable salt of said compound.

7. A pharmaceutical composition, comprising a compound or pharmaceutically acceptable salt according to claim 1 and one or more pharmaceutically acceptable carriers or excipients.

8. A pharmaceutical composition according to claim 7, which is in a form suitable for oral administration or administration by the pulmonary route.

9. A method of treatment of a disease or condition in which HNE is implicated, comprising administering to a subject in need thereof an effective amount of a compound or pharmaceutically acceptable salt according to claim 1,
wherein said disease or condition is chronic obstructive pulmonary disease, bronchiectasis, chronic bronchitis, lung fibrosis, pneumonia, acute respiratory distress syndrome (ARDS), pulmonary emphysema, smoking-induced emphysema, cystic fibrosis, asthma, rhinitis, psoriasis, atopic dermatitis, non-atopic dermatitis, Crohn's disease, ulcerative colitis, or irritable bowel disease.

10. A method of treatment according to claim 9, wherein said disease or condition is chronic obstructive pulmonary disease, bronchiectasis, chronic bronchitis, lung fibrosis, pneumonia, acute respiratory distress syndrome (ARDS), pulmonary emphysema, smoking-induced emphysema, or asthma.

11. A method of treatment according to claim 9, wherein said disease or condition is cystic fibrosis, rhinitis, psoriasis, atopic dermatitis, non-atopic dermatitis, Crohn's disease, ulcerative colitis, or irritable bowel disease.

12. A method of treatment of a disease or condition in which HNE is implicated, comprising administering to a subject in need thereof an effective amount of a compound or pharmaceutically acceptable salt according to claim 6,
wherein said disease or condition is chronic obstructive pulmonary disease, bronchiectasis, chronic bronchitis, lung fibrosis, pneumonia, acute respiratory distress syndrome (ARDS), pulmonary emphysema, smoking-induced emphysema, cystic fibrosis, asthma, rhinitis, psoriasis, atopic dermatitis, non-atopic dermatitis, Crohn's disease, ulcerative colitis, or irritable bowel disease.

13. A method of treatment according to claim 12, wherein said disease or condition is chronic obstructive pulmonary disease, bronchiectasis, chronic bronchitis, lung fibrosis, pneumonia, acute respiratory distress syndrome (ARDS), pulmonary emphysema, smoking-induced emphysema, or asthma.

14. A method of treatment according to claim 12, wherein said disease or condition is cystic fibrosis, rhinitis, psoriasis, atopic dermatitis, non-atopic dermatitis, Crohn's disease, ulcerative colitis, or irritable bowel disease.

\* \* \* \* \*